United States Patent
Ghashghaee

(10) Patent No.: US 10,544,068 B2
(45) Date of Patent: Jan. 28, 2020

(54) CATALYTIC PROCESS FOR PRODUCING OLEFINS

(71) Applicant: Mohammad Ghashghaee, Tehran (IR)

(72) Inventor: Mohammad Ghashghaee, Tehran (IR)

(73) Assignee: IRAN POLYMER AND PETROCHEMICAL INSTITUTE, Tehran (IR)

(*) Notice: Subject to any disclaimer, the term of this patent is extended or adjusted under 35 U.S.C. 154(b) by 0 days.

(21) Appl. No.: 15/650,988

(22) Filed: Jul. 17, 2017

(65) Prior Publication Data

US 2017/0369390 A1 Dec. 28, 2017

Related U.S. Application Data

(60) Provisional application No. 62/375,442, filed on Aug. 16, 2016.

(51) Int. Cl.
| | |
|---|---|
| *C07C 2/12* | (2006.01) |
| *C01B 39/02* | (2006.01) |
| *C10G 50/00* | (2006.01) |
| *B01D 3/00* | (2006.01) |
| *B01J 29/035* | (2006.01) |
| *B01J 29/18* | (2006.01) |
| *B01J 29/08* | (2006.01) |
| *B01J 29/70* | (2006.01) |

(52) U.S. Cl.
CPC ............... *C07C 2/12* (2013.01); *C01B 39/02* (2013.01); *B01D 3/00* (2013.01); *B01J 29/035* (2013.01); *B01J 29/08* (2013.01); *B01J 29/18* (2013.01); *B01J 29/7015* (2013.01); *C10G 50/00* (2013.01)

(58) Field of Classification Search
None
See application file for complete search history.

(56) References Cited

U.S. PATENT DOCUMENTS

| | | | |
|---|---|---|---|
| 5,326,465 A | 7/1994 | Yongqing et al. | |
| 5,358,918 A | 10/1994 | Yukang et al. | |
| 5,672,800 A * | 9/1997 | Mathys .................... | B01J 29/06 585/520 |
| 7,525,002 B2 | 4/2009 | Umansky et al. | |
| 9,193,922 B2 | 11/2015 | Forestiere et al. | |
| 2002/0111523 A1* | 8/2002 | Mathys .................... | C07C 1/20 585/518 |

(Continued)

OTHER PUBLICATIONS

S. Follmann, Influence of the pore architecture on the selective conversion of ethene to propene and butenes over medium pore zeolites, New Journal of Chemistry, Mar. 29, 2016, 40, 4414-4419, Montpellier, France.

(Continued)

*Primary Examiner* — Philip Y Louie
(74) *Attorney, Agent, or Firm* — Bajwa IP Law Firm; Haris Zaheer Bajwa

(57) ABSTRACT

Disclosed herein is a catalytic process for producing higher olefins including three- to four-carbon olefins from ethene sources by producing an ethene-containing stream from an ethene source, and subjecting the ethene-containing stream to a catalytic oligomerization process. In this catalytic process, the catalytic oligomerization process comprises exposing the ethene-containing stream in contact with a catalyst including a mixture of a zeolite material and a zeotype material.

15 Claims, 4 Drawing Sheets

(56) References Cited

U.S. PATENT DOCUMENTS

| | | | |
|---|---|---|---|
| 2004/0030212 A1* | 2/2004 | Al-Soufi | C07C 2/12 585/533 |
| 2011/0124936 A1* | 5/2011 | Cabiac | B01J 29/06 585/514 |
| 2012/0059139 A1 | 3/2012 | Hayashi et al. | |
| 2015/0329438 A1* | 11/2015 | Nyce | C10G 9/00 518/705 |
| 2015/0352538 A1* | 12/2015 | Schoenfeldt | B01J 29/85 502/64 |

OTHER PUBLICATIONS

Linsheng Wang, Conversion of light paraffins for preparing small olefins over ZSM-5 zeolites, Catalysis Letters, Mar. 1994, pp. 61-68, vol. 28, Issue 1.

J.S. Buchanan, The chemistry of olefins production by ZSM-5 addition to catalytic cracking units, Catalysis today, 2000, vol. 55, Issue 3, 207-212.

Sandra Bessell, The conversion of ethene and propene to higher hydrocarbons over ZSM-5, Journal of Catalysis, May 1987, vol. 105, Issue 1, pp. 270-275.

Hiroshi Oikawa, Highly selective conversion of ethene to propene over SAPO-34 as a solid acid catalyst, Applied Catalysis A, 2006, 312, 181-185.

Nazi Rahimi, Catalytic cracking of hydrocarbons over modified ZSM-5 zeolites to produce light olefins, Applied Catalysis, 2011, 398, 1-17.

\* cited by examiner

CATALYTIC PROCESS FOR PRODUCING OLEFINS

CROSS REFERENCE TO RELATED APPLICATION

This application claims the benefit of priority from U.S. Provisional Patent Application Ser. No. 62/375,442, filed on Aug. 16, 2016, and entitled "CATALYTIC PROCESS TO PRODUCE PROPYLENE AND BUTENE," which is incorporated herein by reference in its entirety.

TECHNICAL FIELD

The present disclosure generally relates to the field of catalysts, particularly to a catalytic process for producing olefins, and more particularly to a catalytic process for producing propene and butene.

BACKGROUND

The discovery of new gas fields and the depletion of high quality crude oil resources have resulted in shortages in naphtha, which is a main source of gasoline, and a surplus of light hydrocarbons for conversion and processing. Due to a reduced availability of suitable liquid petroleum feedstocks, olefin units face more stringent conditions in producing valuable three-carbon and four-carbon petrochemicals; thus, alternative methods to conventional steam crackers of naphtha and condensates are required.

Catalytic methods are attractive routes to produce light olefins, such as propene and butene. Given the relative abundance of ethene sources, oligomerization and metathesis routes may be utilized to produce light olefins from ethene as a feedstock. However, catalysts that convert ethene into light olefins through oligomerization face problems, such as poor efficiency, limited operational flexibility, and quick deactivation of the catalyst.

On the other hand, a metathesis route employs a specific composition of ethene and butene as the feedstock. Recent research in this field illustrates that ethene can be directly converted into a mixture of propene and butene in a single operational step. The transition metal catalysts which are employed in the abovementioned metathesis processes, are very sensitive to accompanying poisons of the feed stream. In addition, the use of butene itself as a feed constituent is necessary in these processes.

Accordingly, there is a need in the art for a catalytic process for producing light olefins with improved efficiency and operational flexibility.

SUMMARY

This summary is intended to provide an overview of the subject matter of this disclosure, and is not intended to identify essential elements or key elements of the subject matter, nor is it intended to be used to determine the scope of the claimed implementations. The proper scope of this disclosure may be ascertained from the claims set forth below in view of the detailed description below and the drawings.

In an exemplary embodiment consistent with the present disclosure, a catalytic process producing higher olefins including three- to four-carbon olefins from ethene sources is disclosed. The process may include producing an ethene-containing stream from an ethene source and subjecting the ethene-containing stream to a catalytic oligomerization process. The catalytic oligomerization process comprises exposing the ethene-containing stream in contact with a catalyst including a mixture of a zeolite material and a zeotype material.

In an exemplary embodiment, the catalytic oligomerization process may further include humidifying the ethane-containing stream. Moreover, this catalytic process may further include enriching ethane in the ethene-containing stream.

According to an exemplary embodiment, producing an ethene-containing stream from an ethene source may be done in a process such as a cracking process, dehydrogenation process, and combinations thereof. According to an exemplary embodiment, the ethene source may be selected from paraffinic hydrocarbons, synthetic alcohols, bio-based alcohols, methanol, ethanol, biomass-derived liquid, solid feedstocks, polymer wastes, coal-based materials, syngas, and combinations thereof.

According to an exemplary embodiment, the stream of ethene may include ethene with a concentration of at most 30% of the volume of the ethene stream. Moreover, the ethene stream may have a weight hourly space velocity (WHSV) between 0.1 $h^{-1}$ and 30 $h^{-1}$.

According to an exemplary embodiment, the catalyst may have an active phase that may include components of the catalyst, which are directly participating in the catalytic reaction; therefore, the active phase of the present catalyst may be any components, such as the zeolite material, the zeotype material, and the promoting agent. Furthermore, the active phase may have a zeolite material with a concentration ratio less than 50% of the weight of the active phase.

According to some exemplary embodiment, the zeolite material may be selected from silica or alumina materials or combinations thereof. Moreover, the zeolite material may have a silica to alumina ratio between 3 and 100. In exemplary embodiments, in case of using a second zeolite component, the silica to alumina ratio for that second zeolite component may be between 200 and 2000.

According to an exemplary embodiment, the zeolite material may have a structure as expressed in the codes assigned by the Structure Commission of the International Zeolite Association (IZA); and the structure may be selected from a Chabazite framework (CHA), a Natrolite framework (NAT), a Faujasite framework (FAU), a Mordenite framework (MOR), a beta polymorph A (BEA), ABW, AEL, AFI, AFT, AFW, AFX, AEI, AET, ANA, AWW, CFI, CON, CSV, DFT, EDI, ERI, ETL, ETR, EWT, FER, GIS, IFW, IRY, IRR, IWS, IWW, KFI, LEV, LTA, LTL, LTJ, MEI, MER, MEL, MFI, MTF, MTT, MTW, MWF, MWW, PHI, PSI, RHO, SAF, SAV, SFN, SFS, SFW, SOD, SSO, STT, STW, THO, UOV, UTL, VET, and VFI, or combinations thereof.

According to an exemplary embodiment, the catalyst may have an active phase, and the active phase may have a zeotype material with a concentration ratio less than 50% of the weight of the active phase. The zeotype material may be selected from porous aluminophosphate (AlPO) materials, silicoaluminophosphate (SAPO) materials, analogous materials comprising phosphate constituents, germinate constituents, arsenate constituents, or combinations thereof. Moreover, the zeotype material may have a ratio of alumina and phosphorous to silica between 5 and 400.

According to some exemplary implementations, the zeotype material may have a structure of a Chabazite framework (CHA), a Faujasite framework (FAU), ABW, AEL, AFI, AFR, AFT, AFX, AEI, AET, AHT, ANA, APC, APD, APO, ATT, ATV, AWW, DFO, DFT, EDI, ERI, GIS, LEV, LTA, LTL, MER, PHI, RHO, SAV, SOD, THO, and VFI, or combinations thereof.

According to an exemplary embodiment, the catalyst may further include a promoting agent, a binder, or combinations thereof. The promoting agent may be selected from alkali metals, alkaline earth elements of the groups I and II of the periodic table, or combinations thereof. Moreover, the catalyst may have an active phase, and the active phase may have a promoting agent with a concentration ratio less than 50% of the weight of the active phase.

According to an exemplary embodiment, the binder may include silica particles, silica gel, bentonite particles, alpha alumina, or combinations thereof. Furthermore, the binder may include a mesoporous material, a macroporous material, or combinations thereof.

Other systems, methods, features and advantages of the exemplary embodiments will be, or will become, apparent to one of ordinary skill in the art upon examination of the following figures and the accompanying detailed description. It is intended that all such additional systems, methods, features and advantages be included within this description and this summary, be within the scope of the consistent with exemplary embodiments of the present disclosure, and be protected by the following claims.

BRIEF DESCRIPTION OF THE DRAWINGS

The drawing figures depict one or more implementations in accordance with the present teachings, by way of example only, not by way of limitation. In the figures, like reference numerals refer to the same or similar elements.

DETAILED DESCRIPTION

Figure 1:
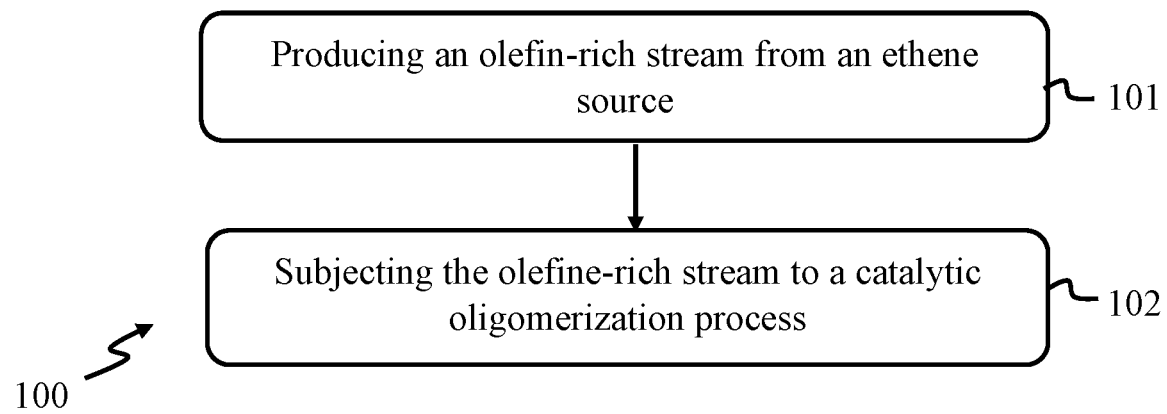
FIG. 1 illustrates a catalytic process for producing higher olefins, such as propene and butene from ethene, consistent with an exemplary embodiment of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

Production of light olefins like propene and butene as raw materials of polymer and petrochemical industries has a great importance. One approach for producing such light olefins may be using ethene as a feedstock for the catalytic production of these materials. The present disclosure is directed to a catalytic process for the conversion of ethene sources into higher olefinic products with a high efficiency, a simple preparation, and with an appropriate stability during the catalytic reaction. The catalytic process may include subjecting a stream of ethene to a catalytic oligomerization process, in which the stream of ethene may be put in contact with a catalyst that may include a mixture of a zeolite material and a zeotype material.

As used herein, the term "zeotype" refers to any members of a family of artificial materials which are based on the structure of zeolites. Moreover, "ethene" is also referred to as "ethylene", and propene is also referred to as "propylene".

The catalytic process of the present disclosure may further include humidifying the ethene-rich stream by using a humidifier, a bubbler, a scrubber, a stream generator, a saturator, a steam injector, a washing tower, or combinations thereof. The stream of ethene may include ethene with a concentration of at most 30% of the volume of the ethene stream. Moreover, the ethene stream may have a weight hourly space velocity (WHSV) of about between 0.1 $h^{-1}$ and 30 $h^{-1}$.

The zeolite material of the catalyst may be selected from materials incorporating silica, alumina, or combinations thereof. Also, the zeolite material may have a silica-to-alumina ratio between 3 and 100. In exemplary embodiments, in case of using a second zeolite component, the silica to alumina ratio for that second zeolite component may be between 200 and 2000. Furthermore, the catalyst may have an active phase and the active phase may have a zeolite material with a concentration ratio less than 50% of the weight of the active phase.

The zeolite material may have a structure as expressed in the codes assigned by the Structure Commission of the International Zeolite Association (IZA); and the structure may be selected from a Chabazite framework (CHA), a Natrolite framework (NAT), a Faujasite framework (FAU), a Mordenite framework (MOR), a beta polymorph A (BEA), ABW, AEL, AFI, AFT, AFW, AFX, AEI, AET, ANA, AWW, CFI, CON, CSV, DFT, EDI, ERI, ETL, ETR, EWT, FER, GIS, IFW, IRY, IRR, IWS, IWW, KFI, LEV, LTA, LTL, LTJ, MEI, MER, MEL, MFI, MTF, MTT, MTW, MWF, MWW, PHI, PSI, RHO, SAF, SAV, SFN, SFS, SFW, SOD, SSO, STT, STW, THO, UOV, UTL, VET, or VFI, and combinations thereof.

The zeotype material of the catalyst may be selected from porous aluminophosphate (AlPO) materials, silicoaluminophosphate (SAPO) materials, and analogous materials involving phosphate constituents, germinate constituents, arsenate constituents, or combinations thereof. Also, the zeotype material may have a ratio of alumina and phosphorous to silica between 5 and 400. The catalyst may have an active phase, and the active phase may have a zeotype material with a concentration ratio less than 50% of the weight of the active phase.

The zeotype material may have a structure of a Chabazite framework (CHA), a Faujasite framework (FAU), ABW, AEL, AFI, AFR, AFT, AFX, AEI, AET, AHT, ANA, APC, APD, APO, ATT, ATV, AWW, DFO, DFT, EDI, ERI, GIS, LEV, LTA, LTL, MER, PHI, RHO, SAV, SOD, THO, and VFI, or combinations thereof.

The catalyst may further include a promoting agent a binder, or a combination thereof. The promoting agent may be selected from alkali metals, alkaline earth elements of the groups I and II of the periodic table, or combinations thereof. Also, the catalyst may have an active phase, and the active phase may have a promoting agent with a concentration ratio less than 50% of the weight of the active phase.

The binder may include silica particles, silica gel, bentonite particles, alpha alumina, or combinations thereof. Also, the binder may be a mesoporous material, a macroporous material, or a combination thereof.

FIG. 1 illustrates a catalytic process or method 100 for producing higher olefins such as propene and butene from ethene, consistent with an exemplary embodiment of the present disclosure. Method 100 may include a step 101 of producing an ethene-containing stream from an ethene source, and a step 102 of subjecting the ethene-containing stream to a catalytic oligomerization process.

In step 101, an ethene-containing stream may be produced from an ethene source by utilizing a conversion process such as cracking or a dehydrogenation process. The ethene source may include any material that may be converted into ethene such as paraffinic hydrocarbons, synthetic or bio-based alcohols, such as methanol and ethanol, biomass-derived liquid or solid feedstocks, polymer wastes, coal-based materials, and syngas, or combinations thereof.

Conversion (i.e, cracking, or dehydrogenation) of the ethene source may be done in an ethene-producing process that may be operated based on any proper technology, such as a thermal cracking, a catalytic cracking, and a catalytic dehydrogenation using a liquid or gaseous feedstock. As a result, the ethene source may be transformed into an ethene-containing stream after an acceptable conversion level in the conversion step.

In step 102, the ethene-containing stream may be subjected to a catalytic oligomerization process, in which the ethene-containing stream may be put in contact with a catalyst including a mixture of a zeolite material and a zeotype material. The catalyst may have an active phase including a zeolite material with a concentration ratio of about less than 50% of the weight of the active phase.

The disclosed catalytic oligomerization process may be based on a hybrid catalyst with a formulation as explained herein. The zeolite material of the catalyst may be selected from silica or alumina materials and combinations thereof; also, the zeolite material may have a silica to alumina ratio between 3 and 100. In exemplary embodiments, in case of using a second zeolite component, the silica to alumina ratio for that second zeolite component may be between 200 and 2000.

The zeotype material of the catalyst may be selected from porous aluminophosphate (AlPO) materials, silicoaluminophosphate (SAPO) materials, and analogous materials involving phosphate constituents, germinate constituents, arsenate constituents, or combinations thereof. Also, the zeotype material may have a ratio of alumina and phosphorous to silica between 5 and 400.

The zeotype material may have a structure of a Chabazite framework (CHA), a Faujasite framework (FAU), ABW, AEL, AFI, AFR, AFT, AFX, AEI, AET, AHT, ANA, APC, APD, APO, ATT, ATV, AWW, DFO, DFT, EDI, ERI, GIS, LEV, LTA, LTL, MER, PHI, RHO, SAV, SOD, THO, and VFI, and combinations thereof. The catalyst may have an active phase including a zeotype material with a concentration ratio of about less than 50% of the weight of the active phase.

The catalyst may further include a promoting agent and a binder. The promoting agent may be selected from alkali metals, alkaline earth elements of the groups I and II of the periodic table, or combinations thereof. Also, the catalyst may have an active phase including a promoting agent with a concentration ratio of about less than 50% of the weight of the active phase.

The binder may include silica particles, silica gel, bentonite particles, alpha alumina or combinations thereof. Also, the binder may be a mesoporous material, a macroporous material, or a combination thereof. The use of binder in the catalyst formulation may be optional, but it may be almost inactive or very poorly active in the catalytic process.

In order to prepare the catalyst formulation, a zeolite material, a zeotype material, and a promoting agent may be intimately grinded or admixed with each other, if needed, within a matrix of binder particles. Moreover, providing the catalytic pellets may be carried out using any techniques such as pelletizing and extrusion to form pellets, tablets, agglomerates, molded forms, extrudates, and the like.

The oligomerization process may be done at the following conditions. At first, the catalyst may be activated. The catalyst activation may be done in a humid or dry atmosphere. The activation atmosphere for activating the catalyst may be any mixture stream of diluted oxygen; and the usual ambient air or a nitrogen-diluted oxygen stream, or even a nitrogen or helium stream, may be chosen as a common activation atmosphere. The activation time of the catalyst may be, for example, between 30 minutes and 10 hours.

After activating the catalyst, the catalytic process for the direct conversion of ethene to propene and butene or higher olefins may be carried out in the gas phase, at low pressure, and in a tandem reaction system; also, the catalytic process may be designed in such a manner that rapid deactivation of the catalyst may be prevented; therefore, ethene-containing stream may enter into the oligomerization reactors for converting ethene to higher olefins, e.g., three- to four-carbon olefins.

The ethene-containing stream as an ethene feedstock may be diluted in a diluent or carrier gas which may be normally helium, nitrogen, argon, carbon dioxide, methane, ethane, light paraffins, and combinations thereof. The ethene concentration in the ethene-containing stream may be lower than 30% and the weight hourly space velocity (WHSV) for the ethene-containing stream may be about between $0.1\ h^{-1}$ and $30\ h^{-1}$. Finally, the product stream may be a stream having significant portions of propene, butene, and a gasoline-range fraction as valuable byproduct.

Figure 2A:
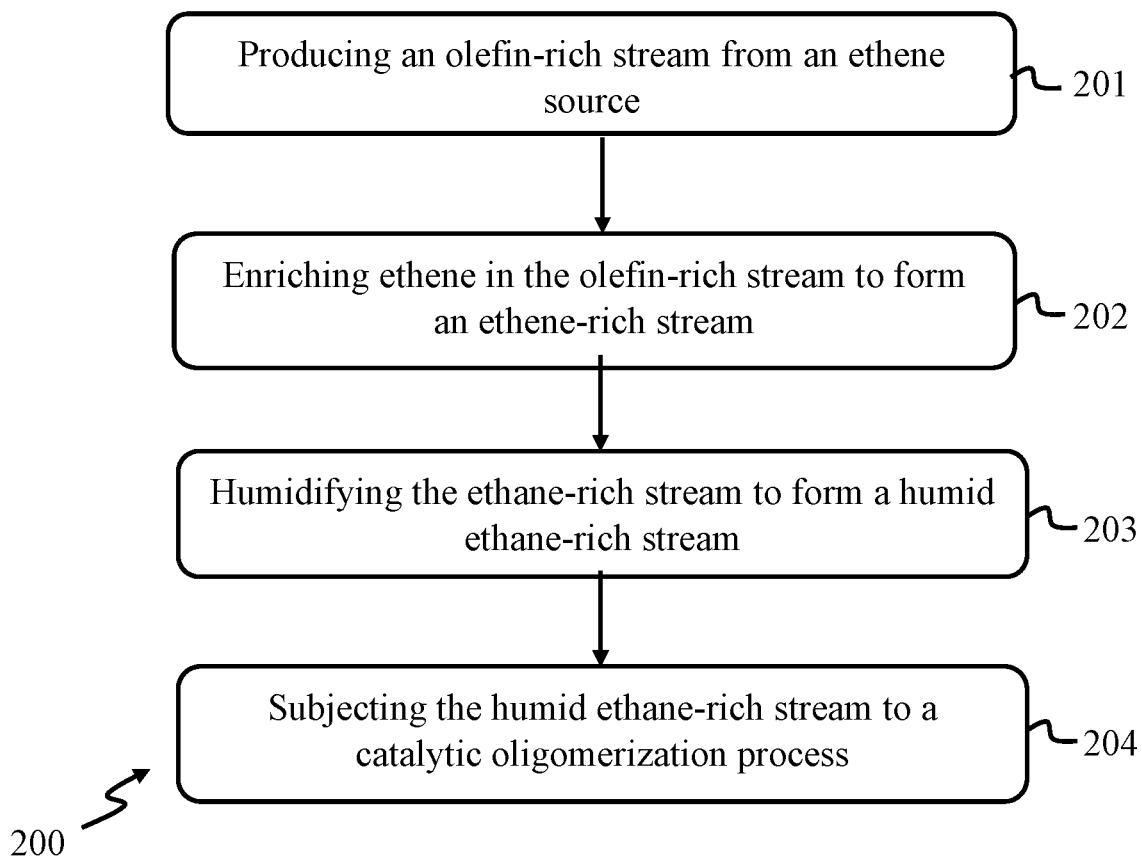
FIG. 2A illustrates a catalytic process for producing higher olefins, such as propene and butene from ethene, consistent with an exemplary embodiment of the present disclosure.

FIG. 2A illustrates a catalytic process or method 200 for producing higher olefins such as propene and butene from ethene, consistent with an exemplary embodiment of the present disclosure. Method 200 may include a step 201 of producing an ethene-containing stream from an ethene source; a step 202 of enriching ethene in the ethene-containing stream to form an ethene-rich stream; a step 203 of humidifying the ethene-rich stream to form a humid ethene-rich stream; and a step 204 of subjecting the humid ethene-rich stream to a catalytic oligomerization process.

In step 201, an ethene-containing stream may be produced from an ethene source in a preliminary conversion process, such as cracking or dehydrogenation. In exemplary embodiments, step 201 may be similar to step 101 of FIG. 1.

In step 202, an ethene-rich stream may be formed by enriching ethene in the ethene-containing stream. Enrichment of the ethene-containing stream may be done by using a separation unit. For example, the ethene-containing stream may be routed to the separation unit for separating an arbitrary part of the produced hydrogen and a part of the injected water, if any, and injected additives, if any, from the ethene-containing stream to form the ethene-rich stream.

In step 203, the produced ethene-rich stream may be humidified to form a humid ethene-rich stream. In an embodiment, humid ethane-rich stream may refer to a stream with a humidity of about at least 1%. Humidifying the ethene-rich stream may be done by a humidifier, a bubbler, a scrubber, a stream generator, a saturator, a steam injector, a washing tower, or combinations thereof.

In step 204, the humid ethene-rich stream may be subjected to a catalytic oligomerization process; therefore, the humid ethene-rich stream may be put in contact with a catalyst including a mixture of a zeolite material and a zeotype material. Furthermore, the catalyst may have an active phase and the active phase may have a zeolite material with a concentration ratio less than 50% of the weight of the active phase.

The proposed catalytic oligomerization process may be done based on a hybrid catalyst with a formulation as explained herein. The zeolite material of the catalyst may be selected from materials incorporating silica, alumina, and combinations thereof also, the zeolite material may have a silica to alumina ratio between 3 and 100. In exemplary embodiments, in case of using a second zeolite component, the silica to alumina ratio for that second zeolite component may be between 200 and 2000.

The zeolite material may have a structure selected from a Chabazite framework (CHA), a Natrolite framework (NAT), a Faujasite framework (FAU), a Mordenite framework (MOR), a beta polymorph A (BEA), ABW, AEL, AFI, AFT, AFW, AFX, AEI, AET, ANA, AWW, CFI, CON, CSV, DFT, EDI, ERI, ETL, ETR, EWT, FER, GIS, IFW, IRY, IRR, IWS, IWW, KFI, LEV, LTA, LTL, LTJ, MEI, MER, MEL, MFI, MTF, MTT, MTW, MWF, MWW, PHI, PSI, RHO, SAF, SAV, SFN, SFS, SFW, SOD, SSO, STT, STW, THO, UOV, UTL, VET, and VFI, or combinations thereof.

The zeotype material of the catalyst may be selected from porous aluminophosphate (AlPO) materials, silicoaluminophosphate (SAPO) materials, and analogous materials involving phosphate constituents, germinate constituents, arsenate constituents, or combinations thereof. Also, the zeotype material may have a ratio of alumina and phosphorous to silica between 5 and 400. The catalyst may have an active phase including a zeotype material with a concentration ratio less than 50% of the weight of the active phase.

The zeotype material may have a structure of a Chabazite framework (CHA), a Faujasite framework (FAU), ABW, AEL, AFI, AFR, AFT, AFX, AEI, AET, AHT, ANA, APC, APD, APO, ATT, ATV, AWW, DFO, DFT, EDI, ERI, GIS, LEV, LTA, LTL, MER, PHI, RHO, SAV, SOD, THO, and VFI, or combinations thereof.

The catalyst may further include a promoting agent, a binder, or combinations thereof. The promoting agent may be selected from alkali metals, alkaline earth elements of the groups I and II of the periodic table, or combinations thereof. Also, the catalyst may have an active phase including a promoting agent with a concentration ratio less than 50% of the weight of the active phase.

The binder may include silica particles, silica gel, bentonite particles, alpha alumina, or combinations thereof. Also, the binder may be a mesoporous material, a macroporous material, or a combination thereof. The use of binder in the catalyst formulation may be optional, but it may be almost inactive or very poorly active in the catalytic process.

In order to prepare the catalyst formulation, a zeolite material, a zeotype material, and a promoting agent may be intimately grinded or admixed with each other, if needed, within a matrix of binder particles. Moreover, providing the catalytic pellets may be carried out using any techniques such as pelletizing and extrusion to form pellets, tablets, agglomerates, molded forms, extrudates, and the like.

The oligomerization process may be done at the following conditions. At first, the catalyst may be activated with an activation stream; the activation atmosphere may be any mixture stream of diluted oxygen in any inert gas; and the usual ambient air, nitrogen stream, or a nitrogen-diluted oxygen stream may be given as a common activation atmosphere. The activation time of the catalyst may be, for example, between 30 minutes and 10 hours.

After activating the catalyst, the catalytic process for the direct conversion of ethene to propene and butene and higher olefins may be carried out in the gas phase, at low pressure, and in a tandem reaction system; also, the catalytic process may be designed in such a manner that rapid deactivation of the catalyst may be prevented.

In order to initiate the catalytic process, the humid ethene-rich stream may be entered into the oligomerization reactors as a feedstock for converting ethene to higher olefins such as three- to four-carbon olefins. The humid ethene-rich stream as an ethene feedstock may be diluted in a diluent or carrier gas which may be normally helium, nitrogen, argon, carbon dioxide, methane, ethane, light paraffin, and combinations thereof.

The ethene concentration in the humid ethene-rich stream may be lower than 30% and the weight hourly space velocity (WHSV) for the humid ethene-rich stream may be about between $0.1\ h^{-1}$ and $30\ h^{-1}$. Finally, after completing the catalytic reaction, the product stream may be taken out from a reactor effluent. The product stream may be a stream having significant portions of propene, butene, and a gasoline-range fraction as valuable byproduct.

Figure 2B:
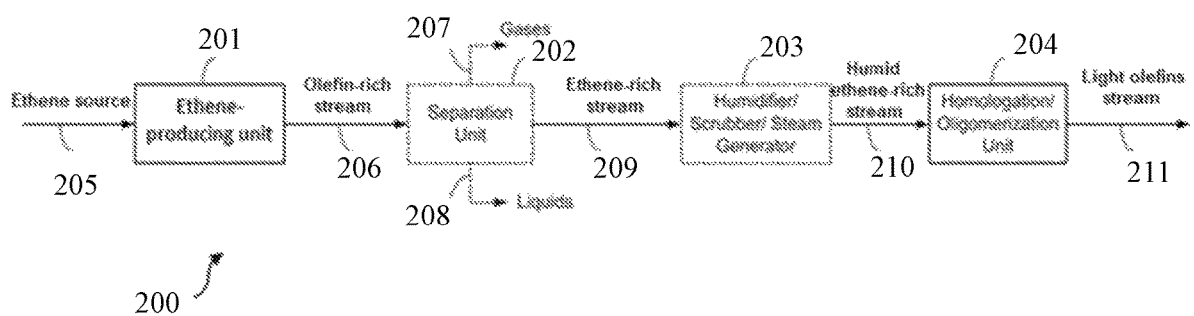
FIG. 2B illustrates a schematic diagram of the catalytic process consistent with an exemplary embodiment of the present disclosure.

FIG. 2B illustrates an exemplary implementation of method 200 that represents a schematic diagram 200 consistent with an exemplary embodiment of the present disclosure. Referring to FIG. 2B, an ethene source material 205, which is convertible to ethene, may enter an ethene-producing unit 201 as a feedstock for producing an olefin-rich stream 206 through a cracking or dehydrogenation process.

In order to enrich ethene in the olefin-rich stream 206, it may be input into a separation unit 202 for removal of any gases 207 or liquids 208; and to obtain a ethene-rich stream 209. The ethene-rich stream 209 may be humidified in a humidifying unit 203 to form a humid ethene-rich stream 210. The humidifying unit may include a humidifier, a scrubber, a steam generator, or combinations thereof.

The humid ethene-rich stream 210 may enter a homologation or an oligomerization unit 204 for converting ethene to higher olefins. After completing the oligomerization process, a product stream 211 including different portions of propene, butene, and other products may be obtained.

EXAMPLES

The following examples describe catalytic processes with different catalyst formulations for producing higher olefins, particularly propene and butene from ethene, according to exemplary implementations of the present disclosure.

Example 1

In this example, a hybrid catalyst for a catalytic process of producing propene and butene from ethene was prepared as follows. The hybrid catalyst having a composition of high silica H-ZSM-5 as a zeolite material, low silica H-ZSM-5 as a zeolite material, H-SAPO-34 as a zeotype material, calcium carbonate ($CaCO_3$) as a promoting agent, and a plurality of silica gel as a binder was prepared as follows.

The high-silica H-ZSM-5 zeolite had an MFI structure and an Si/Al ratio of about 360; also, the high-silica H-ZSM-5 zeolite was present in the catalyst formulation with a concentration ratio of about 24% of the active phase of the catalyst. Moreover, the low-silica H-ZSM-5 zeolite had an MFI structure with an Si/Al ratio of about 38; also, the high-silica H-ZSM-5 zeolite was present in the catalyst formulation with a concentration ratio of about 24% of the active phase of the catalyst.

The H-SAPO-34 zeotype had a CHA structure with an aluminum (Al) and phosphorus (P) to silicon (Si), (Al+P)/Si, ratio of about 8.2; also, the H-SAPO-34 zeotype was present in the catalyst with a concentration ratio of about 24% of the active phase of the catalyst. Moreover, $CaCO_3$ as the promoting agent was present in the catalyst formulation with a concentration ratio of about 28% of the active phase of the catalyst.

In order to prepare the hybrid catalyst, the abovementioned components of the catalysts were perfectly admixed and grinded with each other; and the catalyst pellets were prepared using a pelletizing process. The catalytic experiments were implemented in a micro reactor catalytic setup; and the catalyst pellets were placed between two plugs of quartz wool or silica fibers in a quartz reactor.

In order to activate the catalyst, it was subjected to an air flow as an activation stream with a constant weight hourly space velocity (WHSV) at a predetermined temperature; then, the catalyst was cooled in a nitrogen atmosphere to the reaction temperature and it was kept at these conditions for about 1.5 hours. After that, for initiating the catalytic reaction, the activation stream was replaced with the reacting flow of the feedstock.

In this experiment, the feedstock was a nitrogen-diluted ethene-rich stream. The purity of the gases was over 99.9%; and the molar concentration of ethene in the feedstock was about 12%. Also, the flow rates of the ethene feedstock and the diluting stream of nitrogen were fixed using mass flow controllers (MFCs).

After completing the reactions, a sample was taken from the reactor effluent and it was injected into a gas chromatography (GC) analyzer which was equipped with two detectors of a flame ionization detector (FID) and a thermal conductivity detector (TCD) together with appropriate packed and capillary columns. The experiment was repeated four times at different reaction conditions. TABLE 1 shows the results of the GC analysis of the samples with different reaction conditions such as reaction temperature, pressure, WHSV, and time-on-stream, which means the time elapsed during operation after the reactions started.

TABLE 1

Results of GC analysis of the samples of this experiment.

|  | 1 | 2 | 3 | 4 |
|---|---|---|---|---|
| Conditions |  |  |  |  |
| Reaction temperature, ° C. | 400 | 400 | 500 | 500 |
| Pressure, bar | 1 | 1 | 1 | 1 |
| WHSV, $h^{-1}$ | 9 | 9 | 9 | 9 |
| Time-on-stream, min | 19 | 186 | 33 | 57 |
| Catalytic Performance |  |  |  |  |
| Ethene conversion, % | 78.3 | 69.8 | 70.5 | 68.5 |
| Propene, wt % | 27.3 | 22.8 | 34.6 | 33.8 |
| Butene, wt % | 19.9 | 19.8 | 17.3 | 16.9 |
| Gasoline, wt % | 9.8 | 12.0 | 7.6 | 7.6 |
| Propene + Butene yield, wt % | 47.2 | 43.3 | 51.9 | 50.7 |
| Propene + Butene selectivity, wt % | 60.3 | 62.0 | 73.6 | 74.0 |

According to TABLE 1, the catalyst of this experiment has produced propene and butene from ethene in a catalytic process at a temperature of 500° C. with an average yield of about 51.3 wt %. Also, according to the catalytic performance of the experiment, the average selectivity of propene and butene at the mentioned temperature is about 73.8 wt %. Moreover, increasing the time-on-stream has decreased ethene conversion, and the propene and butene yield; but, it has increased the propene and butene selectivity in the final products.

Figure 3:
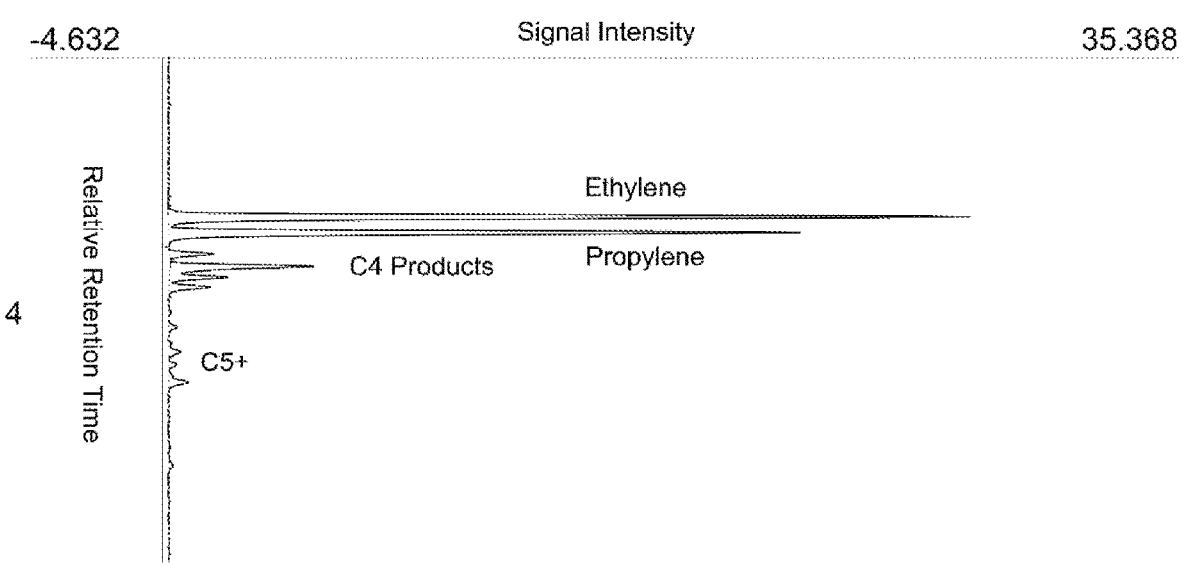
FIG. 3 illustrates a chromatogram of a sample of a product stream as described in connection with EXAMPLE 1.

FIG. 3 shows an exemplary chromatogram of the product stream which was obtained in a catalytic process with the present catalyst formulation at 500° C. and time-on-stream of about 33 minutes. The chromatogram shows the signal intensity versus relative retention time of each specific material.

Referring to FIG. 3, the composition of the sample product stream includes ethene, propene, and C4 products along with a gasoline-range fraction as valuable byproduct. The C4 products were mainly butene isomers. Also, the $C_{5+}$ fraction, which is a fraction having five or more carbon atoms, was taken as gasoline-range byproducts.

Example 2

In this example, a catalyst for a catalytic process of producing propene and butene from ethene was prepared. The catalyst had an active phase of H-SAPO-34 as a zeotype material and calcium carbonate ($CaCO_3$) as a promoting agent.

The H-SAPO-34 zeotype was present in the catalyst with a concentration ratio of about 72% of the active phase of the catalyst. Moreover, $CaCO_3$ as the promoting agent was present in the catalyst with a concentration ratio of about 28% of the active phase of the catalyst. After that, the zeotype material and the promoting agent with silica gel as a binder were mixed perfectly to form a complete catalyst. The catalyst activation and reaction conditions were similar to those in EXAMPLE 1.

After completing the reactions, the samples were taken from the reactor effluent and they were injected into a gas chromatography (GC) analyzer which was equipped with two detectors of a flame ionization detector (FID) and a thermal conductivity detector (TCD) together with appropriate packed and capillary columns. TABLE 2 shows the results of the GC analysis of the samples of product streams with two different reaction conditions.

TABLE 2

Results of GC analysis of the samples of this experiment.

| Conditions |  |  |
|---|---|---|
| Reaction temperature, ° C. | 400 | 400 |
| Pressure, bar | 1 | 1 |
| WHSV, $h^{-1}$ | 9 | 9 |
| Time-on-stream, min | 10 | 130 |
| Catalytic Performance |  |  |
| Ethene conversion, % | 58.7 | 7.7 |
| Propene, wt % | 34.6 | 7.2 |
| Butene, wt % | 9.5 | 0.2 |
| Gasoline, wt % | 13.4 | 12.0 |
| Propene + Butene yield, wt % | 44.1 | 7.4 |
| Propene + Butene selectivity, wt % | 75.1 | 96.2 |

According to TABLE 2, increasing the time-on-stream has decreased ethene conversion, and the propene and butene yield; but, it has increased the propene and butene selectivity in the final products.

Moreover, comparison between the performances of the catalysts of EXAMPLE 1 and this example shows that the average ethene conversion of the catalyst formulation of this experiment is significantly lower than that of the catalyst formulation of EXAMPLE 1; therefore, it can be concluded that the presence of a zeolite component along with a zeotype material in the active phase of the catalyst increases the catalyst efficiency during a long-range operation.

Example 3

In this example, a catalytic process and its catalyst for producing propene and butene from ethene has been described. The catalyst had an active phase having a composition of low-silica H-ZSM-5 as a zeolite material, and calcium carbonate ($CaCO_3$) as a promoting agent.

The low-silica H-ZSM-5 zeolite was present in the catalyst formulation with a concentration ratio of about 72% of the active phase of the catalyst. Moreover, $CaCO_3$ as the promoting agent was present in the catalyst formulation with a concentration ratio of about 28% of the active phase of the catalyst.

After that, the zeolite material and the promoting agent with a plurality of silica gel as a binder were mixed perfectly to form a complete catalyst. The catalyst activation and reaction conditions were similar to those in EXAMPLE 1; but, ethene concentration in the feedstock was chosen to be 5% to prevent from a rapid deactivation of the catalyst.

After completing the reactions, the samples were taken from the reactor effluent and they were injected into a gas chromatography (GC) analyzer which was equipped with two detectors of flame ionization detector (FID) and thermal conductivity detector (TCD) together with appropriate packed and capillary columns. TABLE 3 shows the results of the GC analysis of the sample of the reaction effluent and the catalytic performances of the catalyst.

TABLE 3

Results of the GC analysis of the sample of the reaction and the catalytic performances of the catalyst.

| Conditions | |
|---|---|
| Reaction temperature, ° C. | 400 |
| Pressure, bar | 1 |
| WHSV, $h^{-1}$ | 8 |
| Time-on-stream, min | 33 |
| Catalytic Performance | |
| Ethene conversion, % | 38.5 |
| Propene, wt % | 17.0 |
| Butene, wt % | 8.9 |
| Gasoline, wt % | 6.0 |
| Propene + Butene yield, wt % | 25.9 |
| Propene + Butene selectivity, wt % | 67.3 |

According to TABLE 3, using a catalyst having only a low-silica zeolite component and a promoting agent has decreased the propene and butene yield; therefore, comparison between the catalysts of EXAMPLE 1 and this example illustrates that the catalytic performance data of the catalyst of this example is poorer than the catalyst of EXAMPLE 1; therefore, this indicates that the inclusion of the zeotype constituent may be beneficial in boosting the catalytic performance of the catalyst in the catalytic process.

Example 4

In this example, a catalyst for producing propene and butene from ethene in a catalytic process was prepared. The catalyst included an active phase having a composition of high-silica H-ZSM-5 as a zeolite material, and calcium carbonate ($CaCO_3$) as a promoting agent.

The high-silica H-ZSM-5 zeolite was present in the catalyst with a concentration ratio of about 72% of the active phase of the catalyst. Moreover, $CaCO_3$ as the promoting agent was present in the catalyst with a concentration ratio of about 28% of the active phase of the catalyst.

After that, the zeolite material and the promoting agent with a plurality of silica gel as a binder were mixed perfectly to form a complete catalyst. The catalyst activation and reaction conditions were similar to those in EXAMPLE 1; but, ethene concentration in the feedstock was chosen to be 5% to prevent from a rapid deactivation of the catalyst.

After completing the reactions, a sample was taken from the reactor effluent and it was injected into a gas chromatography (GC) analyzer which was equipped with two detectors of flame ionization detector (FID) and thermal conductivity detector (TCD) together with appropriate packed and capillary columns. TABLE 4 shows the results of the GC analysis of the sample of reaction and the catalytic performances of the catalyst.

TABLE 4

Results of the GC analysis of the sample of the reaction and the catalytic performances of the catalyst.

| Conditions | |
|---|---|
| Reaction temperature, ° C. | 400 |
| Pressure, bar | 1 |
| WHSV, $h^{-1}$ | 8 |
| Time-on-stream, min | 97 |
| Catalytic Performance | |
| Ethene conversion, % | 0.8 |
| Propene, wt % | 0.0 |
| Butene, wt % | 0.4 |
| Gasoline, wt % | 0.1 |
| Propene + Butene yield, wt % | 0.4 |
| Propene + Butene selectivity, wt % | 49.3 |

According to TABLE 4, the catalytic performance is such low that the catalyst may be considered almost inactive to the ethene feedstock; and this data is much lower than the catalytic performance of the catalyst formulation of EXAMPLE 1; this indicates that a proper formulation of the catalyst with the inclusion of the zeotype constituent may be beneficial in boosting the catalytic performance of the catalyst in the process under consideration.

Example 5

In this example, a hybrid catalyst consistent with exemplary embodiments of the present disclosure was prepared; and the catalyst was used in a catalytic process for producing propene and butene from ethene. The hybrid catalyst having a composition of low silica H-ZSM-5 as a zeolite material, H-Y as a zeolite material, H-SAPO-34 as a zeotype material, and a plurality of silica gel as a binder was prepared as follows.

The low-silica H-ZSM-5 zeolite was present in the catalyst with a concentration ratio of about 33% of the active phase of the catalyst. The H-Y zeolite was present in the catalyst with a concentration ratio of about 33% of the active phase of the catalyst. Also, the H-SAPO-34 zeotype was present in the catalyst with a concentration ratio of about 34% of the active phase of the catalyst.

After that, the zeolite materials and zeotype material with silica gel as the binder were mixed perfectly to form a complete catalyst. The catalyst activation and the reaction conditions were similar to those in EXAMPLE 1; but, ethene concentration in the feedstock was chosen to be 5% to prevent from a rapid deactivation of the catalyst.

After completing the reactions, two samples were taken from the reactor effluent and they were injected into a gas chromatography (GC) analyzer with two detectors of flame ionization detector (FID) and thermal conductivity detector (TCD) together with appropriate packed and capillary columns. TABLE 5 shows the results of the GC analysis of the samples of reactions with different reaction conditions and their catalytic performances.

TABLE 5

Results of the GC analysis of the sample of the reaction and the catalytic performances of the catalyst.

| Conditions | | |
|---|---|---|
| Reaction temperature, °C. | 400 | 400 |
| Pressure, bar | 1 | 1 |
| WHSV, $h^{-1}$ | 12 | 12 |
| Time-on-stream, min | 21 | 80 |
| Catalytic Performance | | |
| Ethene conversion, % | 17.9 | 49.5 |
| Propene, wt % | 11.1 | 8.4 |
| Butene, wt % | 4.5 | 12.9 |
| Gasoline, wt % | 0.6 | 26.0 |
| Propene + Butene yield, wt % | 15.6 | 21.3 |
| Propene + Butene selectivity, wt % | 87.1 | 43.1 |

According to TABLE 5, the average ethene conversion and average yields of propene and butene were lower than those in EXAMPLE 1. This indicates that the replacement of the high-silica H-ZSM-5 zeolite, with a MFI framework, and the calcium carbonate ($CaCO_3$) as the promoting agent, with an H-Y zeolite decreased both ethene conversion and light olefins yield. However, the gasoline yield was increased with this catalyst formulation compared to that with the catalyst formulation of EXAMPLE 1.

Example 6

In this example, a catalyst for producing propene and butene from ethene in a catalytic process was prepared. The catalyst had an active phase having a composition of low-silica H-ZSM-5 as a zeolite material, and H-SAPO-34 as a zeotype material.

The low-silica H-ZSM-5 zeolite was present in the catalyst with a concentration ratio of about 50% of the active phase of the catalyst. Moreover, H-SAPO-34 zeotype was present in the catalyst with a concentration ratio of about 50% of the active phase of the catalyst.

After that, the zeolite material and the zeotype material with a plurality of silica gel as a binder were mixed perfectly to form a complete catalyst. The catalyst activation and the reaction conditions were similar to those in EXAMPLE 1; but, ethene concentration in the feedstock was chosen to be 5% to prevent from a rapid deactivation of the catalyst.

After completing the reactions, four samples were taken from the reactor effluent and they were injected into a gas chromatography (GC) analyzer which was equipped with two detectors of flame ionization detector (FID) and thermal conductivity detector (TCD) together with appropriate packed and capillary columns. TABLE 6 shows the results of the GC analysis of the sample of reaction and the catalytic performances of the catalyst.

TABLE 6

Results of the GC analysis of the sample of the reaction and the catalytic performances of the catalyst.

| Conditions | | | | |
|---|---|---|---|---|
| Reaction temperature, °C. | 400 | 400 | 400 | 400 |
| Pressure, bar | 1 | 1 | 1 | 1 |
| WHSV, $h^{-1}$ | 18 | 18 | 18 | 18 |
| Carrier gas | $N_2$ | $N_2$ | $CO_2$ | $CO_2$ |
| Time-on-stream, min | 9 | 42 | 87 | 137 |
| Catalytic Performance | | | | |
| Ethene conversion, % | 55.6 | 60.5 | 51.7 | 44.7 |
| Propene, wt % | 26.4 | 25.8 | 22.2 | 19.8 |
| Butene, wt % | 12.3 | 13.6 | 9.2 | 8.8 |
| Gasoline, wt % | 6.5 | 9.7 | 11.6 | 7.2 |
| Propene + Butene yield, wt % | 38.8 | 39.4 | 31.4 | 28.6 |
| Propene + Butene selectivity, wt % | 69.6 | 65.1 | 60.7 | 63.9 |

According to TABLE 6, the average ethene conversion and average yields of propene and butene were lower than those in EXAMPLE 1; therefore, the omission of low-silica zeolite and the promoting agent from the formulation given in EXAMPLE 1 may be detrimental; and the catalyst formulation may benefit from a synergistic interplay of its different components.

Moreover, TABLE 6 illustrates that the replacement of the carrier gas with other available gases may be feasible with little influence on the performance of the catalyst in the said process.

Example 7

In this example, a catalyst for producing propene and butene from ethene in a catalytic process was prepared. The catalyst had an active phase having a composition of H-MOR as a zeolite material, and USY as another zeolite material.

The H-MOR zeolite has an MOR framework and it was present in the catalyst formulation with a concentration ratio of about 50% of the active phase of the catalyst. Moreover, USY zeolite had an FAU framework structure and it was present in the catalyst formulation with a concentration ratio of about 50% of the active phase of the catalyst.

After that, the zeolite materials with a plurality of silica gel as a binder were mixed perfectly to form a complete catalyst. Catalyst activation and reaction conditions were similar to those in EXAMPLE 1.

After completing the reactions, two samples were taken from the reactor effluent and injected into a gas chromatography (GC) analyzer which was equipped with two detectors of flame ionization detector (FID) and thermal conductivity detector (TCD) together with appropriate packed and capillary columns. TABLE 7 shows the results of the GC analysis of the sample of reaction and the catalytic performances of the catalyst.

TABLE 7

Results of the GC analysis of the sample of the reaction and the catalytic performances of the catalyst.

| Conditions | | |
|---|---|---|
| Reaction temperature, °C. | 400 | 400 |
| Pressure, bar | 1 | 1 |
| WHSV, $h^{-1}$ | 18 | 18 |
| Time-on-stream, min | 9 | 28 |

TABLE 7-continued

Results of the GC analysis of the sample of the reaction and the catalytic performances of the catalyst.

| Catalytic Performance | | |
|---|---|---|
| Ethene conversion, % | 47.9 | 6.0 |
| Propene, wt % | 30.1 | 3.7 |
| Butene, wt % | 2.0 | 0.3 |
| Gasoline, wt % | 0.0 | 0.0 |
| Propene + Butene yield, wt % | 32.1 | 4.0 |
| Propene + Butene selectivity, wt % | 67.0 | 66.7 |

According to TABLE 7, the average performance of the catalyst is not as high as that in EXAMPLE 1; therefore, the catalyst formulation of EXAMPLE 1 may be more efficient than the catalyst formulation of the present example by providing a higher ethene conversion and higher yields of propene and butene in the long range.

Example 8

In this example, regeneration of a catalyst which was used in a catalytic process was examined; therefore, a spent sample of the hybrid catalyst of EXAMPLE 1 was regenerated in an air stream with a WHSV of about 3.9 $h^{-1}$ at a temperature of about 600° C. for a duration of about 15 hours; and then, the catalyst was cooled in a nitrogen atmosphere to the reaction temperature and kept for 1 hour at these conditions. After regenerating the spent catalyst, the reacting flow was replaced for the activation stream. Catalyst activation and reaction conditions were similar to those in EXAMPLE 1.

After completing the reactions, one sample was taken from the reactor effluent and it was injected into a gas chromatography (GC) analyzer which was equipped with two detectors of flame ionization detector (FID) and thermal conductivity detector (TCD) together with appropriate packed and capillary columns. TABLE 8 shows the results of the GC analysis of the sample of reaction and the catalytic performances of the regenerated catalyst.

TABLE 8

Results of the GC analysis of the sample of the reaction and the catalytic performances of the regenerated catalyst.

| Conditions | |
|---|---|
| Reaction temperature, ° C. | 400 |
| Pressure, bar | 1 |
| WHSV, $h^{-1}$ | 9 |
| Time-on-stream, min | 10 |
| Catalytic Performance | |
| Ethene conversion, % | 70 |
| Propene, wt % | 27 |
| Butene, wt % | 16 |
| Gasoline, wt % | 9 |
| Propene + Butene yield, wt % | 43 |
| Propene + Butene selectivity, wt % | 61 |

According to TABLE 8, the spent catalyst of EXAMPLE 1 may be regenerated with the procedure of the present example to retrieve the initial activity of about 90% of ethene conversion with almost no significant loss in the propene yield and propene and butene selectivity.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A catalytic process for producing three- to four-carbon olefins from ethene sources, comprising:
   producing an ethene-containing stream from an ethene source;
   forming a humid ethene-rich stream with a humidity of at least 1% by humidifying the ethene-containing stream; and
   subjecting the humid ethene-rich stream to a catalytic oligomerization process comprising:
      producing the three- to four-carbon olefins by exposing the humid ethene-rich stream to a catalyst comprising:
         a zeolite material comprising:
            a low-silica zeolite material with a silica to alumina ratio between 3 and 100 at a concentration of greater than 0 and less than 50 percent of the weight of an active phase of the catalyst; and
            a high-silica zeolite material with a silica to alumina ratio of at least 200 at a concentration of greater than 0 and less than 50 percent of the weight of the active phase of the catalyst; and
         a zeotype material with a ratio of alumina and phosphorous to silica between 5 and 400 and a concentration of greater than 0 and less than 50 percent of the weight of the active phase of the catalyst.

2. The catalytic process according to claim 1, further comprising enriching ethene in the ethene-containing stream.

3. The catalytic process according to claim 1, wherein producing an ethene-containing stream from an ethene source is done via a process selected from a group consisting of a cracking process, dehydrogenation process, and combinations thereof.

4. The catalytic process according to claim 1, wherein the ethene source is selected from a group consisting of paraffinic hydrocarbons, synthetic alcohols, bio-based alcohols, methanol, ethanol, biomass-derived liquid or solid feedstocks, polymer wastes, coal-based materials, syngas, and combinations thereof.

5. The catalytic process according to claim 1, wherein the ethene-containing stream includes ethene with a concentration of at most 30% of the volume of the ethene stream.

6. The catalytic process according to claim 1, wherein the ethene-containing stream is exposed to the catalyst at a weight hourly space velocity (WHSV) between $0.1\ h^{-1}$ and $30\ h^{-1}$.

7. The catalytic process according to claim 1, wherein the zeolite material is selected from the group consisting of silica, alumina, and combinations thereof.

8. The catalytic process according to claim 1, wherein the zeolite material has a structure selected from the group consisting of a Chabazite framework (CHA), a Natrolite framework (NAT), a Faujasite framework (FAU), a Mordenite framework (MOR), a beta polymorph A (BEA), ABW, AEL, AFI, AFT, AFW, AFX, AEI, AET, ANA, AWW, CFI, CON, CSV, DFT, EDI, ERI, ETL, ETR, EWT, FER, GIS, IFW, IRY, IRR, IWS, IWW, KFI, LEV, LTA, LTL, LTJ, MEI, MER, MEL, MFI, MTF, MTT, MTW, MWF, MWW, PHI, PSI, RHO, SAF, SAV, SFN, SFS, SFW, SOD, SSO, STT, STW, THO, UOV, UTL, VET, VFI, and combinations thereof.

9. The catalytic process according to claim 1, wherein the zeotype material is selected from the group consisting of porous aluminophosphate (AlPO) materials, silicoaluminophosphate (SAPO) materials, and materials comprising phosphate constituents, germinate constituents, arsenate constituents, and combinations thereof.

10. The process of claim 1, wherein the zeotype material has a structure selected from the group consisting of a Chabazite framework (CHA), a Faujasite framework (FAU), ABW, AEL, AFI, AFR, AFT, AFX, AEI, AET, AHT, ANA, APC, APD, APO, ATT, ATV, AWW, DFO, DFT, EDI, ERI, GIS, LEV, LTA, LTL, MER, PHI, RHO, SAV, SOD, THO, VFI, and combinations thereof.

11. The catalytic process according to claim 1, wherein the catalyst further comprises a promoting agent and a binder.

12. The catalytic process according to claim 11, wherein the active phase has a promoting agent with a concentration ratio more than 20% and less than 50% of the weight of the active phase.

13. The catalytic process according to claim 11, wherein the promoting agent comprises alkali metals, alkaline earth elements of the groups I and II of the periodic table, or combinations thereof.

14. The catalytic process according to claim 11, wherein the binder comprises silica particles, silica gel, bentonite particles, alpha alumina, or combinations thereof.

15. The catalytic process according to claim 11, wherein the binder is selected from the group consisting of a mesoporous material, a macroporous material, and combinations thereof.

* * * * *